United States Patent
Gogol, Jr.

(10) Patent No.: US 9,506,895 B2
(45) Date of Patent: Nov. 29, 2016

(54) COMBINED CRYSTAL RETAINER AND CONTACT SYSTEM FOR DEPOSITION MONITOR SENSORS

(71) Applicant: Inficon, Inc., East Syracuse, NY (US)

(72) Inventor: Carl A. Gogol, Jr., Manlius, NY (US)

(73) Assignee: INFICON, INC., East Syracuse, NY (US)

( * ) Notice: Subject to any disclaimer, the term of this patent is extended or adjusted under 35 U.S.C. 154(b) by 853 days.

(21) Appl. No.: 13/896,775

(22) Filed: May 17, 2013

(65) Prior Publication Data

US 2014/0340098 A1   Nov. 20, 2014

(51) Int. Cl.
   *G01R 27/28* (2006.01)
   *G01N 29/24* (2006.01)
   *H01L 41/047* (2006.01)
   *H01L 41/053* (2006.01)

(52) U.S. Cl.
   CPC ....... *G01N 29/2443* (2013.01); *H01L 41/0475* (2013.01); *H01L 41/053* (2013.01)

(58) Field of Classification Search
   CPC . G01R 1/0416; G01R 1/07307; G01F 1/115; G02F 1/1339; H01L 21/68764; G01N 33/54373
   USPC .......... 324/649, 200, 207.13, 219, 220, 234, 324/242–247, 500, 529, 530, 760.01, 727, 324/76.49, 76.11
   See application file for complete search history.

(56) References Cited

U.S. PATENT DOCUMENTS

| | | | | |
|---|---|---|---|---|
| 2,408,768 A | * | 10/1946 | Fox | H03H 9/1007 310/348 |
| 5,117,192 A | | 5/1992 | Hurd | |
| 5,174,164 A | * | 12/1992 | Wilheim | F22B 37/003 324/220 |
| 2006/0141608 A1 | * | 6/2006 | Aastrup | G01N 29/036 435/287.1 |

OTHER PUBLICATIONS

Applications of Piezoelectric Quartz Crystal Microbalances; by C. Lu and A.W. Czanderna; Elsevier, First Edition; 42 pgs.

* cited by examiner

*Primary Examiner* — Vincent Q Nguyen
*Assistant Examiner* — Trung Nguyen
(74) *Attorney, Agent, or Firm* — Barclay Damon, LLP

(57) ABSTRACT

A combination retainer and electrical contact mechanism for a deposition monitor sensor includes a sensor body and a removable flexible electrical contact spanning between a fixed electrical (contact) element in the sensor's body and one face of an associated monitor crystal. A retainer insulates or insures electrical isolation of the spanning electrical contact from unwanted contact to electrically grounded components in which at least one of the retainer and crystal holder include features that maintain the electrical contact with the retainer in order to provide a single mechanism.

19 Claims, 5 Drawing Sheets

COMBINED CRYSTAL RETAINER AND CONTACT SYSTEM FOR DEPOSITION MONITOR SENSORS

TECHNICAL FIELD

This application relates generally to the field of material processing and more specifically to a combined monitor crystal retainer and electrical contact system, as well as a related method for retaining a monitor crystal while providing electrical contact therewith for use in deposition monitor sensors.

BACKGROUND AND SUMMARY

A quartz crystal microbalance is often used as part of a control system in order to optimize the production of specialty thin film coatings that may be used for a wide variety of functional and decorative uses. Exemplary uses of these film coatings cover a fairly wide spectrum that may include those aimed at increasing a machine component's wear resistance, narrow band optical filtering for increasing optical communication channels or spectral based chemical analysis, enhancement of light transmission through lenses and windows, and enhancing the reflection of mirrors and reducing the light reflected from a transparent surface or simply to apply a color; e.g. create a low cost substitute for gold color, among a myriad of other possible uses. The quartz crystal microbalance that is used for optimizing these processes is commonly known as a deposition process controller. A deposition process controller is used for real time sensing of the precise amount of material that is incident onto and subsequently adheres to a face of a resonantly vibrating piezoelectric crystal. The deposition parameters commonly sensed with this technology are the rate of deposition and total thickness. The crystal microbalance's sensor function relates to the frequency reduction of the composite resonator (monitor crystal plus deposited material) caused by the mass added to the vibrating piezoelectric plate that is partially exposed to the deposition. The foregoing application has a generally well-accepted formulation and is clearly described in chapter 2 of "Applications of Piezoelectric Quartz Crystal Microbalances" by Lu and Czanderna (Elsevier, first edition pp. 19-57) the entire contents of which are herein incorporated. In practice, the quartz crystal microbalance is located among or nearby the substrates that are being coated and is used as a surrogate substrate, allowing for precise inference of the amount of material added to the substrates by careful calculation based on the directional distribution of the material leaving a deposition source and use of the geometric relationships between the deposition source, substrates and the monitor crystal.

The precise and accurate measurement of the monitor crystal's frequency is an essential component of deposition control. The measurement of frequency is commonly accomplished according to two (2) basic techniques or methods. The first technique is referred to as the so called "active" method in which the monitor crystal and its adlayer becomes part of an oscillator circuit and the resulting frequency is measured by one of many possible ways of measuring frequency. One commonly employed method used to measure frequency employs an independent precision reference oscillator of known frequency to establish a precise and repetitive period of time by counting this oscillator's pulses to a predetermined fixed number. This process of repeatedly counting a fixed number of the precision oscillator's pulses establishes an exactly recurring period of time. A second counter is started and stopped by this recurring period that similarly measures the pulses from the resonating monitor crystal. This method of counting the number of measurement crystal pulses over a fixed period of time permits a very accurate measurement of the monitor crystal's frequency and is commonly known as the "period measurement technique". The change of the monitor crystal's frequency is related to the mass added, so therefore knowing the density of the added material, the thickness may be inferred. Noting the change of thickness between successive recurring measurement periods, the rate of material deposition may then be calculated. This measured deposition rate is often used as the measured variable in a control system that manipulates the power to the deposition source such that the deposition rate can be stabilized or in some cases changed and manipulated in desired and advantageous ways.

The second common technique of determining the monitor crystal's frequency is considered a "passive" method that is described in detail, for example, in U.S. Pat. No. 5,117,192 to Hurd, the contents of which are herein incorporated. In the Hurd method, the monitor crystal is excited with a voltage of specific frequency and the related current response of the piezoelectric monitor crystal to this specific frequency is detected as being either capacitive, inductive or in-phase, the latter which is indicative of zero phase shift and infers the composite resonator (piezoelectric crystal plus coating(s) is operating at the desired series resonance point. Using the teachings of Hurd, the result of the phase measurement can be very rapidly converted to an intelligently calculated new applied interrogation frequency. Knowledge of the nature (i.e., sign and magnitude) of the monitor crystal's phase error response is used to calculate the next interrogation frequency, so that in only a few interrogation cycles the series resonance of the monitor crystal can be determined with very low error, even if material deposition is taking place and the frequency is simultaneously rapidly changing in response to the mass of material that is being added.

The measurement of frequency by each of the above methods are improved by minimizing sources of noise and insuring the circuits to and from the monitor crystal are low resistance, thereby further insuring the effective Q (i.e., the quality factor of the monitor crystal) can be maintained at a high level, during which as much deposition material may be added as is possible. When the effective crystal Q deteriorates, the measurement circuits are substantially less able to make a consistent frequency measurement and the control system is compromised by this source of noise. The adherence and growth of the deposition material on the monitor crystal is, by its nature, a dissipative process due to its lack of piezoelectric contribution, acoustic dissipation due to crystalline defects, and in many cases the introduction of tensile or compressive stresses to the composite resonator.

Essential requirements of a deposition monitor sensor constructed for commercial use include highly repeatable low noise and low resistance electrical connections, easy replacement of the monitor crystal, and product design of the sensor to insure that the deposition material being monitored and controlled is excluded from those areas that might compromise electrical isolation and integrity. The sharpness of the monitor crystal's resonance, which is related to the quality factor Q, is known to be reduced as the amount of deposition material is increased on the face of the monitor crystal and this loss of Q is known to increase the perceived noise of the measurement. When the noise reaches a level sufficient to make the measurement noise larger than that which can be tolerated by the process, replacement of the monitor crystal is necessitated. Any improvements taken to reduce the electrical resistance or shield the circuit elements from deposition or from other deterioration mechanisms, such as surface or interface corrosion, will have a positive effect on the measurement including lower noise and sometimes increased life of the monitor crystal.

To further clarify the needs outlined above, it must be understood that the electrical elements in the circuit used to apply the interrogation voltage waveform stimulating the monitor crystal and the subsequent sensing of the resulting current's phase relationship to that applied voltage waveform should have low resistance and the contacts and wires should be shielded from being coated by the material being applied. This is clearly required in the passive measurement technique and a necessary, but less obvious, requirement for any active measurement scheme. Loss of signal strength due to high resistance from loose or corroded connections or a parasitic electrical leak caused by conductive or capacitive leakage through deposited material from the applied radio frequency voltage and the return path allows a portion of the voltage to bypass the monitor crystal and is thereby detrimental to the optimal function of the measurement circuit.

In the prior art, the most common means of making electrical contact with a supported monitor crystal is to employ two separate spring contact assemblies or systems, often of the leaf type. Using two contact systems in series allows the user to have a convenient crystal holder package that can be simply and entirely removed from the deposition sensor for subsequent cleaning and monitor crystal replenishment without concern for the monitor crystal either falling out of a receiving cavity of the holder package, or otherwise tilting or hanging up and becoming broken during insertion into the receiving cavity.

In a known and typical dual contact scheme, a first leaf spring contact is used to make direct contact with one face (electrode) of a monitor crystal retained within a crystal holder and in which the first spring contact simultaneously pushes the monitor crystal onto an annular seat of the crystal holder. The first leaf spring contact is electrically connected to a conductive plate, allowing a second leaf spring contact, which is physically and electrically fixed to the deposition sensor body to be electrically connected to the first leaf spring contact when the holder assembly is physically inserted into the sensor body. Another intermediate conductive element then completes the electrical circuit to the detection/driving system of the deposition controller.

Clearly, a single leaf spring contact system having fewer pieces and contact junctions would be electrically superior, but without a retainer to hold the monitor crystal in proper relationship to its desired position in the crystal holder package all of the aforementioned practical problems associated with monitor crystal replacement are strongly manifested. When the positioning of the monitor crystal's face with the holder's crystal seat is not automatically aided by the local gravity field and instead the local gravity field tends to tilt or dislodge the monitor crystal, the installation or removal of the holder package becomes extremely difficult. One known early design that was successful in eliminating contacts, but was problematic regarding the replacement of the monitor crystal in hard to reach or gravity challenged positions, is typified in Lu's FIGS. 17a & b of the aforementioned book by Lu and Czanderna at page 53 thereof.

It is logical to assume that when any process is difficult and unpleasant, it is more likely to be performed improperly than when the process is easy and simple. For these reasons, it is common for most crystal sensor contact systems to include a retainer and accept the drawbacks of higher cost and slightly diminished electrical conduction properties in order to ease the above-referred to replacement task. The basic two contact system discussed herein has been employed successfully for more than 40 years.

The present invention minimizes the detrimental resistive effects of having numerous electrical contacts in series with the monitor crystal but without losing the convenient, orientation independent crystal holder package that is provided by using a retainer component. This desired electrical conduction benefit is manifested in a way that limits the potential for monitor crystal damage, while still providing secure placement of the monitor crystal within the holder package for insertion into the sensor that is orientation independent. The disclosed invention also provides a means of quickly and easily renewing the electrical contact system without hand tools or a need to solder in-situ. While it may be possible to add a retainer component to a design, such as that disclosed by Lu et al., it is found in practice that the spring contact used to make contact with the monitor crystal is susceptible to damage during routine cleaning; for example, a vacuum cleaning nozzle wiping across the sensor's holder cavity and reaching the contact spring causing distortion or breakage. The replacement of the contact spring requires tools, and or soldering and has to be performed in a position that is often difficult to reach or in an orientation that makes replacement and removal times long and frustrating. If soldering is required to repair the spring, the associated use of flux is a further complication because the applied flux must be thoroughly and meticulously removed after soldering and before processing can resume in order to avoid flux-caused contamination of the coating process and apparatus.

As a result, it can now be clearly seen that an invention that incorporates a retainer's function along with a means of reducing the number of electrical contacts, while fostering easy and quick in-situ replacement of any electrical contact system without tools or soldering is a very desirable improvement.

Therefore and according to one version, there is provided a combination retainer and electrical contact mechanism for a deposition monitor sensor, said mechanism comprising a sensor body and a monitor crystal retained within a crystal holder package. A removable flexible electrical contact spans between a fixed electrical contact element in the sensor body and a face of the retained monitor crystal. The mechanism further includes at least one insulating/isolating element in which the removable flexible electrical contact is associated with the at least one insulating/isolating element to provide a single mechanism.

In one version, the flexible electrical contact is defined by a coiled conductive spring having a first diameter section extending over a portion of its length and a second diameter section, which is larger than the first diameter section, defined over a separate portion. According to at least one version, the second diameter section is sized to engage a retention feature, such as an annular groove, formed within the insulating/isolating element.

The coiled conductive wire spring can be made from an electrically conductive wire. For example, the electrically conductive wire can be selected from the group consisting of stainless steel, piano wire, Inconel, beryllium copper, nickel copper and molybdenum, and in which each may be coated with gold or other contact enhancing material.

According to another embodiment, the removable flexible electrical contact can comprise a tubular body having leaf springs attached at respective ends thereof. The tubular body can include a first diameter section over a portion of its length and a second diameter section over another portion of its length, the second diameter section being sized for retention within an internal groove of the retainer. In one version, a split ring is disposed to engage the internal groove with the second diameter section.

In some versions, the retainer can be defined by a hollow cylindrical member having a split gap over its circumference, enabling the retainer to reduce its effective diameter when compressed. When the compressive force is removed, the retainer is configured to releasably engage an inner wall defining an axial bore of the crystal holder.

Alternatively, the retainer according to at least one embodiment can include a set of externally disposed ears that are configured to engage receiving slots defined in the crystal holder. The receiving slots include circumferential groove portions, enabling the retainer to be releasably secured to the crystal holder by rotating the retainer as engaged with the slot(s). As such, the retainer maintains a relatively light friction or interference fit within the machined bore of the crystal holder and provides a modest level of retention for the monitor crystal as the contained spanning electrical contact (e.g. spring) engages the crystal and creates friction.

The retainer can be made from an insulating material such as ceramic or a rigid plastic with acceptable process temperature and outgassing qualities, such as PEEK.

According to another version, there is provided a method for retaining a monitor crystal and providing electrical contact therewith for use in a deposition control monitor, said method comprising the step of providing a crystal holder having an axial bore and an annular seat sized for receiving a monitor crystal. According to this method, a retainer is disposed between the crystal holder and a sensor body, the retainer being at least partially disposed in the axial bore of the crystal bore and the sensor body including a fixed electrical contact engaged with an electrical source of the deposition control monitor. A releasable flexible spanning electrical contact is engaged between a fixed electrical contact of the sensor body and one face of a retained monitor crystal, wherein at least one of the crystal holder and the retainer includes at least one feature for maintaining the spanning electrical contact in a fixed orientation.

In one embodiment, the removable flexible spanning electrical contact includes a first diameter section over a portion of its length and a second diameter portion over another portion of its length. The second diameter section is configured to engage an internal groove provided in the retainer.

In some embodiments, the flexible electrical contact is a coiled conductive spring having respective ends configured to engage a fixed electrical contact of the sensor body and the face of the retained monitor crystal, respectively. In another version, the flexible electrical contact is defined by a tubular conductive body having leaf springs attached at opposing ends of the tubular body.

In some versions, the retainer can be defined by a hollow cylindrical member having a split gap over its circumference, enabling the retainer to reduce its effective diameter when compressed. When the compressive force is removed, the retainer is configured to releasably engage an inner wall defining an axial bore of the crystal holder.

Alternatively, the retainer according to at least one embodiment can include a set of externally disposed ears that are configured to engage receiving slots defined in the crystal holder. The receiving slots include arcuate or circumferential grooved portions, enabling the retainer to be releasably secured to the crystal holder by means of a twisting action once engaged. As such, the retainer maintains a relatively light friction or interference fit within the machined bore of the crystal holder and provides a modest level of retention for the monitor crystal.

One advantage provided by the herein described combination contact/retainer system is that fewer components are required, reducing the overall number of components as well as related costs in manufacture and replacement. The reduction in the total number of parts and at least some machined features are eliminated, thereby creating a much simpler and more reliable apparatus.

Another related advantage is an overall reduction in the number of electrical interfaces in the monitor crystal sensor, which reduces the voltage drop due to contact resistance.

In addition, maintenance of sensors is simplified herein by eliminating the need to solder at least some replacement items, eliminate removal and replacement of screws, and avoiding the necessity to remove the entire sensor assembly from the vacuum coating tool to do this.

Still further, convenience of positive retention of the monitor crystal within the crystal holder assembly is provided, thereby easing the process of removal and replacement of monitor crystals by eliminating concern for having to make contact with the monitor crystal's surface and minimizing the possibility of breakage of the monitor crystal while performing these routine operations.

In addition, a crystal retainer is introduced that can provide the function of restraining the monitor crystal in the crystal holder, while allowing a contact spring device to pass through the holder unimpeded.

These and other features and advantages will be readily apparent from the following Detailed Description, which should be read in conjunction with the accompanying drawings.

DETAILED DESCRIPTION

The following description relates to several embodiments of a system for retaining a monitor crystal that is used in conjunction with a deposition process monitor, the system further insuring electrical contact between an electrical source and a face of a retained monitor crystal, such as a piezoelectric crystal. Throughout the course of discussion, several terms are used in order to describe the invention in accordance with the accompanying drawings. These terms, such as "front", "rear", "lateral", "upper", "lower", "proximal", "distal" and the like are merely intended to provide a suitable frame of reference with regard to the accompanying drawings. These terms are not intended to otherwise inhibit the scope of the present invention, including the claims. In addition, the included drawings are not necessarily to scale and are simply intended to clearly illustrate the salient features of the invention.

Figure 1:
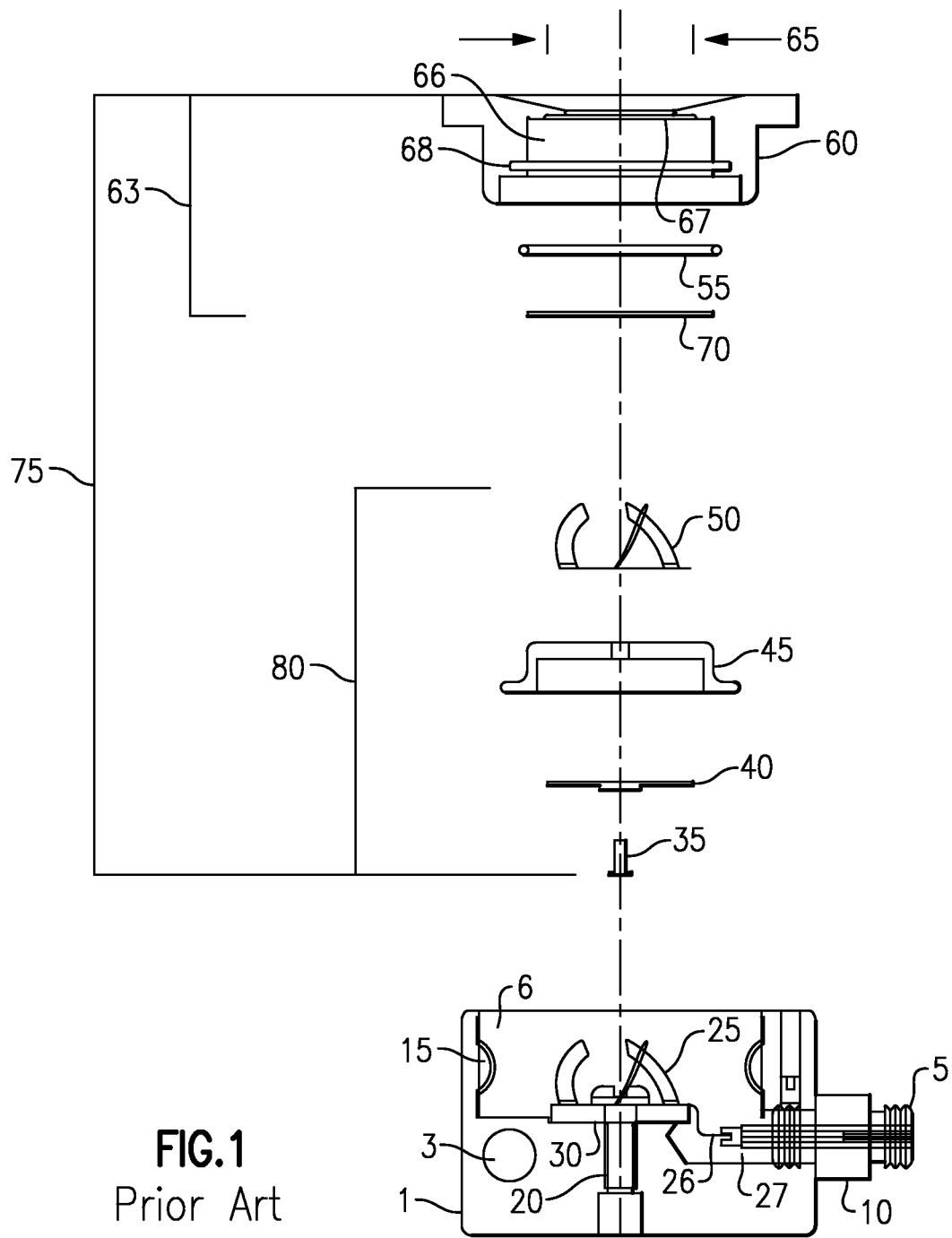
FIG. 1 is an exploded elevational view of a prior or known dual contact monitor crystal retention and electrical contact system for use in a material deposition sensor.

A typical prior art version of a deposition sensor that incorporates a retainer is shown in FIG. 1 and depicted as a cross-sectional view of a typical sensor body 1 with an integral water passage 3 that is used to provide a fluid passage for the purposes of cooling, heating or temperature control depending on the nature and temperature of the fluid flowing within. The fluid is typically brought to the sensor body 1 and removed after flowing through the integral passage 3 by a suitable number of small tubes (not shown) that are interconnected to the passage 3 and sealed. A male/female coaxial cable connector 5 disposed in relation to a retaining cavity 4 of the sensor body 1 provides a means of easy electrical connection/disconnection to the deposition controller's exciting and detection circuitry (not shown). In this exemplary illustration, the male/female coaxial electrical connector 5 is locked into position with a set screw 10 to avoid back out when a mating coaxial electrical connector (not shown) is removed. A leaf spring with tail 25 is mounted to the sensor body 1 with a non-conducting screw 20 and is further electrically isolated by an intervening insulator disk 30. Electrical connection to the leaf spring with tail 25 is made by routing the tail to the center pin 6 of the male/female coaxial cable connector 5 and soldering, or alternatively, a spring contact (not shown) or spot welding can be used. Depending on the physical clearance to the sensor body 1, an insulator over the tail of the leaf spring 25 may or may not be required.

Still referring to FIG. 1, a crystal holder and retainer assembly 75 includes two distinct subassemblies; namely, a crystal holder subassembly 63 and a retainer subassembly 80 that combine to maintain a monitor crystal 70, such as a piezoelectric quartz crystal, seated in proper position and in good electrical contact within an axial machined bore 66 of a substantially cylindrical crystal holder body 60 of the crystal holder subassembly 63. Each subassembly is ultimately configured to provide flat and intimate contact with an annular seat 67 provided at the end of the axial machined bore 66 of the crystal holder body 60 and against which the monitor crystal 70 is retained. The crystal holder body 60 is made from a material such as stainless steel and includes a pair of opposing ends connected by the axial bore 66. The monitor crystal 70 and retainer subassembly 80 engage one end of the crystal holder body 60, while the opposite end defines a material aperture 65 that enables exposure of the remaining side of the monitor crystal to the deposition chamber (not shown).

The retainer subassembly 80 provides all-orientation mechanical retention of the monitor crystal 70 and also transfers the electrical connection from the leaf spring 25 to the monitor crystal 70. The retainer subassembly 80 consists of an insulating retainer body 45 that can be made from a ceramic or rigid machinable plastic such as PEEK, that is designed to slide into the axial bore 66 machined within the crystal holder body 60 while an expanding wire retainer 55 is sized for insertion within an annular retainer groove 61 formed within an inner wall of the axial bore 66 and is hereafter firmly restrained until intentional removal. The retainer subassembly 80 is constructed by inserting a conducting rivet 35 through a center hole formed in a contact disk 40, through the hole 46 in the center of the insulating retainer body 45 and through the center of a leaf spring 50. Finally, the conducting rivet 35 is carefully deformed to insure good electrical contact and long term mechanical integrity. In place of mechanical deformation, the conducting rivet 35 is sometimes soldered.

In the prior art crystal holder/retainer assembly 75 herein described, the electrical circuit to and from the male/female coaxial cable connector 5 encounters numerous joints and connections. More specifically and from the coaxial connector's center post 27, a solder joint 26 connects to the leaf spring with tail 25, which makes physical contact with the contact disk 40, which in turn makes contact to the conducting rivet 35, and which then makes contact with the leaf spring 50. Finally, the leaf spring 50 makes contact with the piezoelectric monitor crystal 70, thereby requiring a total of (5) five separate electrical contacts and junctions.

Figure 2A:
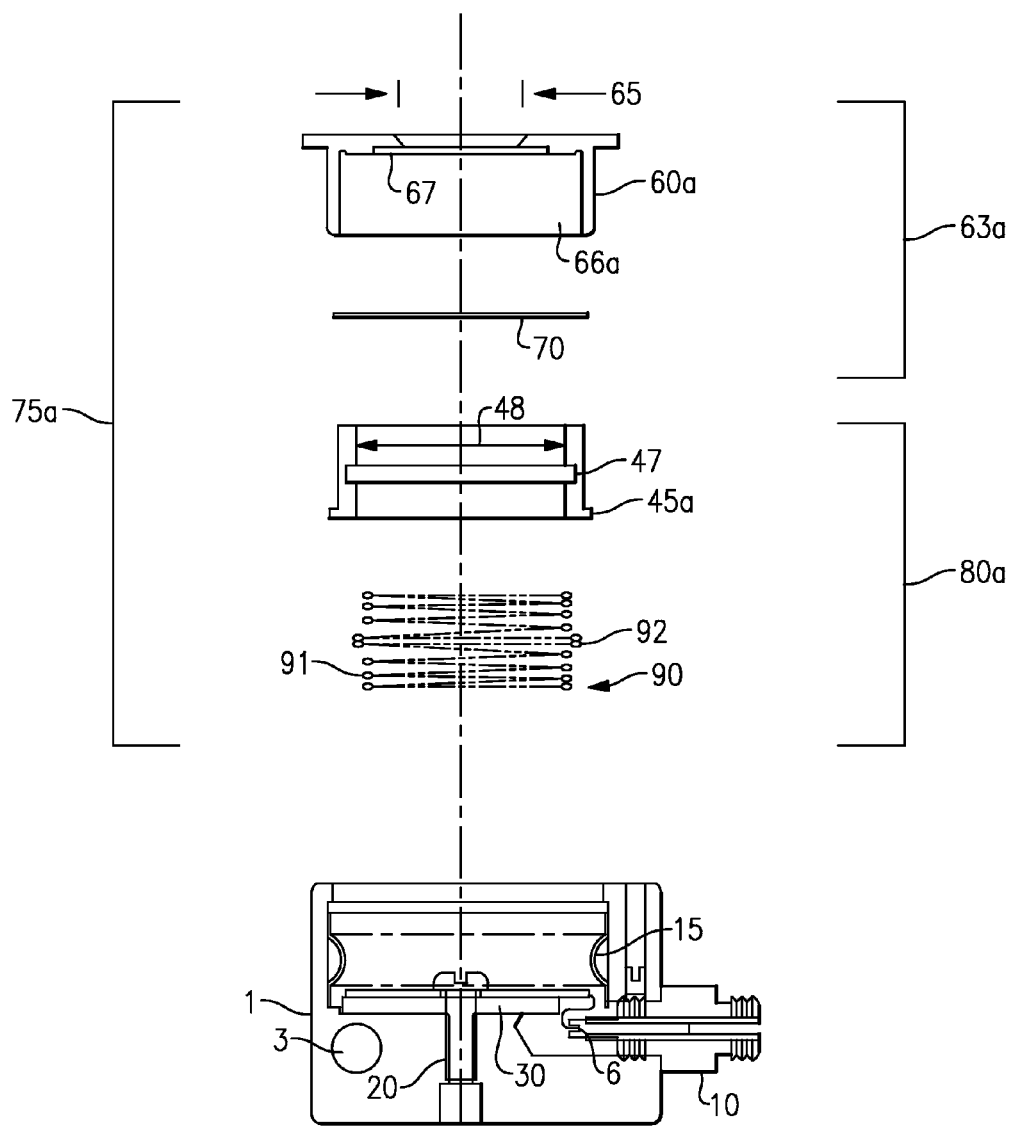
FIG. 2(a) is an exploded side elevational view of a combination monitor crystal retention and electrical contact apparatus in accordance with an exemplary embodiment.
Figure 2B:
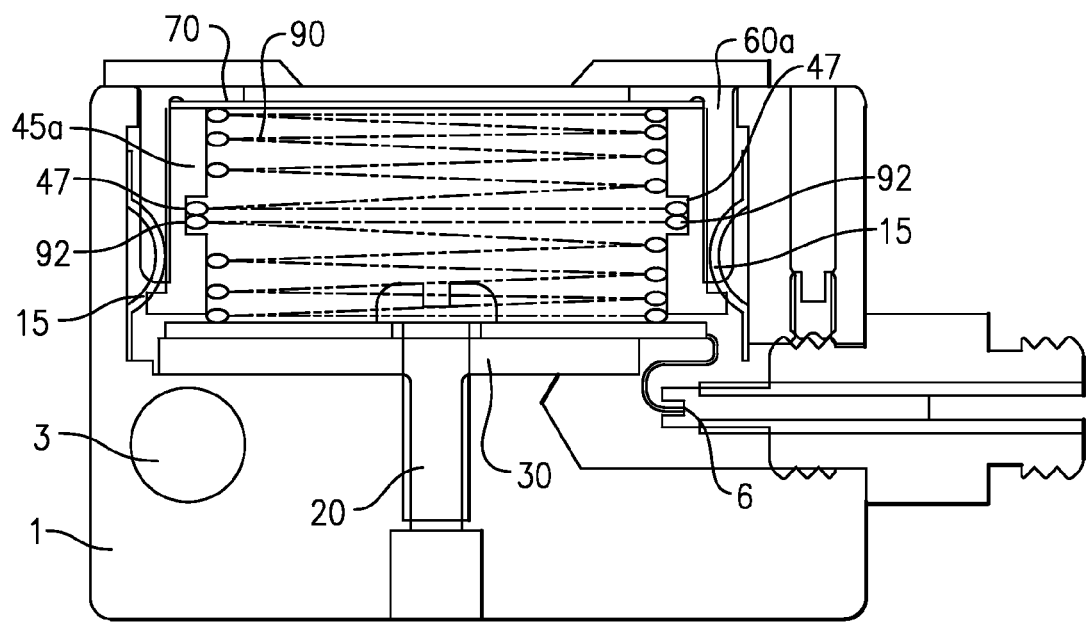
FIG. 2(b) is an assembled side elevational view of the combination monitor crystal retention and electrical contact apparatus of FIG. 2(a)

With the foregoing background, a design in accordance with an exemplary embodiment is herein depicted in FIGS. 2(a) and 2(b) in a manner that parallels the description of the known assembly 75 shown above. Many features and functions are identical to those depicted in FIG. 1, or are at least functionally equivalent, with some small variation and therefore similar parts are herein labeled with the same reference numerals for the sake of clarity.

FIG. 2(a) provides a cross-sectional view of a typical sensor body 1 having an integral water passage 3 that is used to provide a fluid passage for the purposes of cooling, heating or temperature control depending on the nature and temperature of the fluid flowing within. The fluid is typically brought to the sensor body 1 and removed after flowing through the integral passage 3 by small tubes (not shown) connecting to the sensor body 1. A male/female coaxial cable electrical connector 5 is used to provide a means of easy electrical connection/disconnection to the exciting and detection circuitry (not shown). In this exemplary embodiment, the coaxial cable electrical connector 5 is locked into position using a set screw 10 to avoid back out when the mating coaxial connector (not shown) is removed. In lieu of the first leaf spring 25, FIG. 1, a flat contact plate with tail 25a is mounted to the sensor body 1 with a non-conducting screw 20 and is further electrically isolated by an intervening insulator disk 30. Electrical connection of the flat contact plate 25a is made by routing the integral tail of the plate 25a to the coaxial connector's center pin 6 and soldering or in some cases a spring contact or spot welding is used. Depending on physical clearance to the sensor body 1, an insulator over the tail may or may not be necessary.

A crystal holder and retainer assembly 75a is defined by a pair of subassemblies, namely a crystal holder subassembly 63a and a retainer subassembly 80a, respectively, used to maintain a monitor crystal 70, such as a piezoelectric quartz crystal, in proper position/orientation and in good electrical contact within a substantially cylindrical crystal holder body 60 by maintaining flat and intimate contact against an annular seat 67 defined at the end of a machined axial bore 66 of the cylindrical crystal holder body 60. The holder and retainer assembly 75a provides mechanical retention of the monitor crystal 70 and also transfers the electrical connection from the flat contact plate with tail 25a to the monitor crystal 70.

More specifically and according to this exemplary embodiment, the retainer subassembly 80*a* comprises an insulating retainer body 45*a* having a hollow substantially cylindrical configuration including a pair of opposing ends and a coiled spring contact 90. The coiled spring contact 90 is defined by respective ends and is preferably made from an electrically conductive wire made from, but not limited to stainless steel, Inconel, beryllium copper, nickel copper, piano wire or molybdenum. The coiled spring contact 90 is defined by a first diameter region 91 extending over a substantial portion of its overall length and a second expanded diameter region 92 extending over an intermediate portion of the length of the spring contact. The second diameter region 92 has a slightly larger diameter designed to protrude into an annular retention groove 47 which is formed within an inner wall of the hollow insulating retainer body 45*a*. For purposes of operation, the expanded second diameter region 92 needs only to be sufficiently enlarged to provide retention within the annular retention groove 47 of the retainer 45*a* to avoid the casual separation of the coiled spring contact 90 by gravity or normal movement during use. In this way, the coiled spring contact 90 may be easily removed by applying modest separation forces and can be easily replaced, as needed, within the retention groove 47. According to this exemplary embodiment, the insulating retainer body 45*a* is made from a resilient, low outgassing and machineable plastic or other insulator that is compatible with high purity process vacuums. As discussed herein and briefly referring to FIGS. 3(*a*) and 3(*b*), the retainer body 45*a* is designed according to one version with a split gap 49, FIG. 3(*b*) along its circumference, enabling the retainer body 45*a* to be slightly compressed radially to permit insertion into the machined axial bore 66 of the crystal holder body 60 and in which removal of the compressive force on the retainer body 45*a* restores the retainer body 45*a* to attempt to assume its original size by radial expansion and in compressive contact with the crystal bore 68 of the crystal holder 60. In this way, the function of the holder's wire spring retainer 55 of the prior known version can be directly incorporated into the retainer body 45*a*, thereby eliminating the need for a wire spring retainer and its necessary groove 68.

The herein described retainer subassembly 80*a* can be assembled by inserting the coiled conducting spring contact 90 so that the second diameter region 92 is intentionally made to a larger diameter than the outermost turns and is positively retained in the annular retention groove 47 of the retainer body 45*a*. This expanded region 92 according to this version extends over approximately two turns of the spring contact 90, but providing this region over a single turn or more than two turns would also be sufficient to meet the intended purpose. The retention of the coil spring contact 90 within the insulating retainer body 45*a* is not essential to function, but is a user convenience that reduces the number of individual pieces that typically have to be accounted for when replacing the monitor crystal 70.

In the improved assembly described herein, the electrical circuit to and from the coaxial cable connector encounters fewer joints and connections. Summarily and from the coaxial cable connector's center post 27, a solder joint 26 connects to the integral tail of the flat contact plate 25*a*, which makes physical contact to one circular face of the coil spring contact 90, while the other circular face of the coiled conductive spring 90 makes contact with a face of the monitor crystal 70 retained against the annular seat 67 of the crystal holder body 60 for a total of three (3) separate contacts, or two (2) fewer than that of known retention/contact system versions including those depicted in FIG. 1.

The electrical return path from the opposite side (face) of the monitor crystal 70 is through physical contact with the annular seat 67, which is an integral portion of the crystal holder body 60 at the end of the axial bore 66*a*, and then being forced against a deformable spring 15 that is provided in the inner wall of the receiving cavity 4 of the sensor body 1, wherein the deformable spring makes intimate contact with the sensor body 1 and then finally by contact to the shell of coaxial cable connector 5 being aided by the set screw 10. The return electrical path described in this embodiment is literally identical in both the previously known and improved designs. Similarly, the signal is connected to the excitation and measurement circuits (not shown) of the deposition controller (not shown) through a mating coaxial cable connector and coaxial cable in both the current and improved designs and in which the monitor crystal can be excited and resonated by known techniques, as previously described.

Figure 3A:
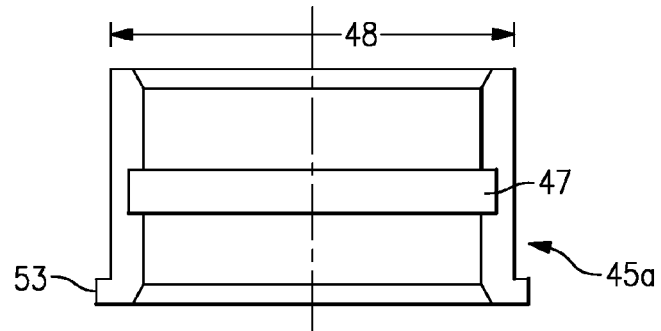
FIG. 3(a) is a side elevational view of a retainer used in the combination system and in accordance with one exemplary embodiment.
Figure 3B:
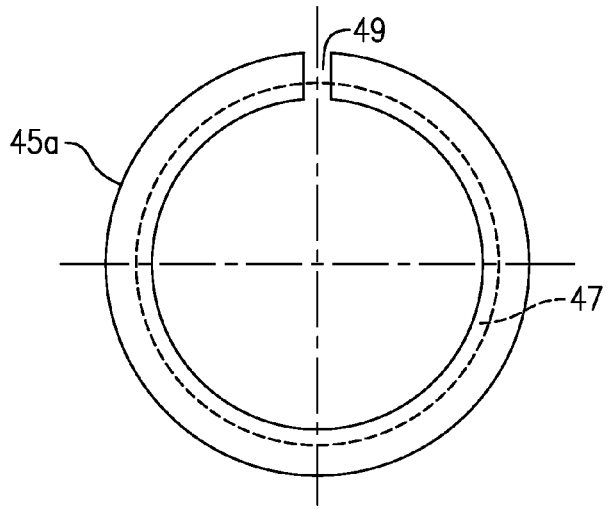
FIG. 3(b) is a plan view of the retainer of FIG. 3(a)

As noted, FIGS. 3(*a*) and 3(*b*) depict respective cross sectional and plan views of the retainer body 45*a* in accordance with an exemplary embodiment. The retainer body 45*a* is made from an insulating material such as a ceramic, rigid plastic or other suitable material and is defined by a substantially cylindrical configuration with a pair of open ends and an inner diameter 48, which is manufactured slightly larger than the axial bore 66 machined in the crystal holder body 60. According to this embodiment, the outer diameter 48 is approximately 0.005 to 0.010 inches larger when machined, but any diameter slightly larger than the axial bore 66 but still capable of entering the axial bore 66 will work in a way that although not ideal, can be considered functional. Even if the outer diameter 48 is slightly smaller, it will in practice exhibit some small retention capability due to misalignment induced friction with the bore. The cylindrical retainer body 45*a* according to this embodiment is normally completely machined in all other ways before the retainer's split gap 49 is added, insuring good roundness and finish on all features. The width of the split gap 49 is typically about 0.020" to about 0.032", and chosen so standard and readily available cutters might be used. A slightly smaller gap might also be used, as long as the cylindrical retainer body 45*a* can be squeezed sufficiently circumferentially to enter the axial machined bore 66 of the crystal holder body 60. A larger gap might also be used with a limitation to not make it overly large to the point that the cylindrical retainer body 45*a* would lose its ability to self-center within the axial bore 66 of the crystal holder body 60 and consequently allow spring contact 90 to contact the inner wall of the axial bore 66, shorting the electrical circuit.

Figure 4:
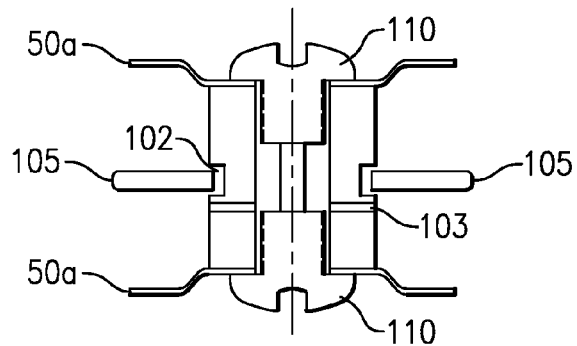
FIG. 4 is a side elevational view of a spanning electrical contact of the combination system and in accordance with an alternative construction.

FIG. 4 shows a cross sectional view of an alternate construction for an electrical contact 99 that uses essentially the same cylindrical retainer body 45*a*, as previously described. According to this alternate version, two leaf springs 50*a* are captured by two screws 110 that are threaded into respective ends of an electrically conductive contact body 100 and thereby completing electrical continuity between the two individual leaf springs 50*a*. The contact body 100 must be electrically conductive and is preferably hollow. While not essential that the entire length of the tubular contact body 100 be hollow, the feature must extend sufficiently on each side to be conveniently threaded in extent to engage the screws 110 completely and insure tightness of the leaf springs 50*a* for good electrical contact. At least one vent hole 103 is drilled into the contact body 100. It is easier to provide the entire length of the contact body 100 as hollow in order to cross-drill into the formed volume only once rather than having to provide one vent hole 103 for each end. The purpose of the drilled vent hole 103 is to allow easy passage of retained atmospheric or process gasses into the vacuum vessel and avoid a condition known as virtual leaking, which is well known and can create contamination. This contamination delays the process of complete evacuation of the processing chamber to high vacuum, thereby further delaying the start of processing. An external retainer groove 102 is provided as a second diameter section of the tubular body 100, this retainer groove 102 being designed to loosely engage one of many types of snap or split rings 105 in order to provide and maintain at least a loose fastening between the insulating retainer groove 47 and the contact body 100. As noted and in use, this alternative electrical contact 99 can be provided in lieu of the coiled spring contact 90. In use, one of the leaf springs 50b will make contact with the fixed electrical contact of the sensor body (not shown in this view), while the remaining leaf spring 50a will contact one face of the monitor crystal 70, FIG. 2(b), as retained within the defined axial bore 66 of the crystal holder body 60. The return path using this electrical contact 99 is unchanged from that previously described.

FIGS. 5(a), 5(b) and 6(a), 6(b), taken together, describe another alternative design for the crystal holder and retainer subassemblies, respectively. These alternative subassembly designs do not necessarily rely on the resiliency of the retainer material or a separate spring for retention of same within the machined axial bore 66 extending through a substantially cylindrical crystal holder body 60b. In this specific version, it is necessary for the inner diameter 48a of the crystal holder body 60b to be somewhat less than the axial machined bore 66 thereof in order to freely pass. More specifically, the retainer body 45b, which is a substantially cylindrical and hollow member does not include a split gap 49, but is defined by at least one radially outwardly projecting retainer ear 52 that is configured and sized to engage a crystal holder body 60b through at least one receiving slot 54 defined therein for retaining an ear 54.

Figure 5A:
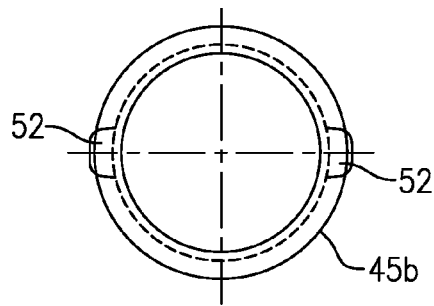
FIG. 5(a) is a plan view of a retainer in accordance with another exemplary embodiment.
Figure 5B:
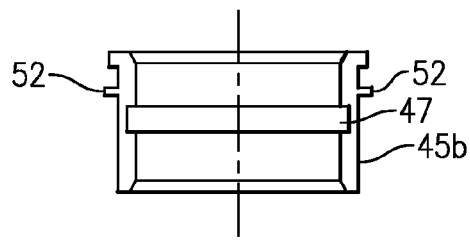
FIG. 5(b) is a side elevational view of the retainer of FIG. 5(a)
Figure 6A:
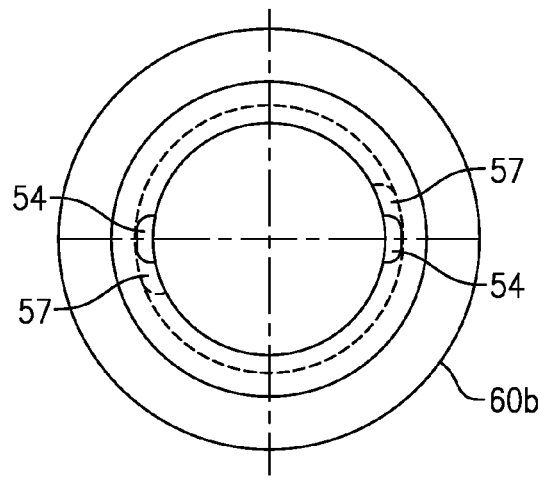
FIG. 6(a) is a plan view of a crystal holder body made in accordance with an exemplary embodiment for use with the retainer of FIGS. 5(a) and 5(b)
Figure 6B:
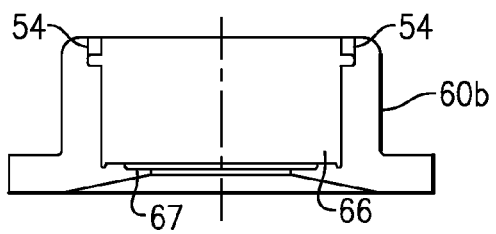
FIG. 6(b) is a side elevational view of the crystal holder body of FIG. 6(a).

As shown in FIGS. 5(a) and 5(b), the cylindrical hollow retainer body 45 includes a pair of diametrically opposed retainer ears 52 that project radially from the exterior of the retainer body 45b and are sized and configured for engagement within a corresponding pair of receiving slots 54 provided in the inner wall of the axial bore 66 of the crystal holder body 60b. Each of the receiving slots 54 extend from the end of the crystal holder body 60 opposite the material aperture 65, the receiving slots 54 further including an enclosed arcuate or circumferential grooved portion 57. When assembled, the receiving slots 54 permit retention of the retainer body 45b when a small angular twist of the retainer body 45b is made about its primary axis in a predetermined (e.g., counterclockwise) direction, releasably securing the retainer ears 52 within corresponding arcuate grooved portions 57 of the receiving slots 54. Disassembly can be easily performed by rotating the retainer body 45b in the opposite (e.g., clockwise) direction so as to align the retainer ears 52 with the receiving slots 54 and then axially withdrawing the insulating retainer body 45b. There is no imperative for a tight or close fit of the retainer ears 54 within the defined arcuate grooved portion 57 as the tension that the coil spring contact 90, FIG. 2(b), generates from contacting the retained monitor crystal 70, FIG. 2(b), will have a natural tendency to provide a reaction force so that sufficient friction will be present to avoid rotation during the activity necessary to insert the combined assembly into the sensor body 1, FIG. 2(b), to engage the deformable spring 15, FIG. 2(b). Once the retainer body 45b is fully inserted in the sensor body 1 and even though the retainer and holder ears 54 are coincidently aligned, there will be no loss of electrical function as the coiled contact spring 90 is compressed between the piezoelectric monitor crystal 70, FIG. 2(b), and the flat contact plate 24, FIG. 2(b), respectively, the monitor crystal 70 being firmly engaged against the defined annular seat 67 of the crystal holder body 60b.

PARTS LIST FOR FIGS. 1-6(b)

1 sensor body
1a sensor body with holder threads
3 integral fluid passage
4 retaining cavity
5 male/female coaxial cable connector
6 center pin, connector
10 set screw
15 deformable spring
20 non-conducting screw
24 flat contact plate with tail
25 leaf spring with tail
26 solder joint
27 center conductor
30 Insulator disk
35 conducting rivet
40 contact disk
45 insulating retainer body
45a insulating retainer body
45b insulating retainer body
46 hole
47 insulating retainer groove
48 insulating retainer outer diameter
48a retainer outer diameter
49 retainer split gap
50 leaf spring
50a leaf spring
52 retainer ear
53 retainer lip
54 receiving slot for retainer ear(s)
55 retainer wire spring
57 arcuate or circumferential grooved portions, receiving slot
60 crystal holder
60b crystal holder
60a crystal holder
60c crystal holder
63 crystal holder subassembly
63a crystal holder subassembly
65 material aperture
66 crystal bore
67 annular seat
68 retention groove, retainer
70 monitor crystal
74 crystal holder assembly
75 crystal holder and retainer assembly
75a crystal holder and retainer assembly
75b crystal holder assembly
80 retainer subassembly
80a retainer subassembly
90 coil spring contact
91 first diameter portion
92 second diameter portion
99 contact, electrical
102 external retainer groove
103 vent 105 split ring
110 screw It will be readily apparent that other modifications and variations will be readily apparent based on the teachings of this disclosure, and in accordance with the following claims.

The invention claimed is:

1. A combination retainer and electrical contact mechanism for use in a deposition monitor sensor, said mechanism comprising:
   a sensor body having a fixed electrical contact disposed therein;
   a monitor crystal;
   a crystal holder configured for retaining said monitor crystal within an axial bore, said crystal holder being engaged within a receiving cavity of said sensor body;
   a removable flexible contact spanning between the fixed electrical contact element in the sensor body and one face of the retained monitor crystal such that the removable flexible contact directly contacts both the fixed electrical contact element and the face of the retained monitor crystal; and
   a retainer configured for insulating or insuring electrical isolation of the removable flexible electrical contact and in which at least one retainer and said flexible electrical contact includes at least one feature for securably maintaining said flexible removable electrical contact.

2. The system as recited in claim 1, further comprising means for substantially retaining the monitor crystal in a predetermined position within the crystal holder independent of orientation relative to a local gravity field.

3. The system as recited in claim 1, wherein said retainer is made from an insulating material and configured for allowing the through passage of said removable flexible electrical contact, said retainer being in fixed relation to the sensor body.

4. The system as recited in claim 1, wherein said retainer includes at least one feature for retaining the removable flexible electrical contact and maintaining contact therewith.

5. The system as recited in claim 1, wherein said flexible electrical contact comprises a coiled conductive wire spring having a pair of opposing axial ends, one end contacting the face of said retained monitor crystal and the remaining end contacting the fixed electrical contact in said sensor body.

6. The system as recited in claim 5, wherein said coiled conductive wire spring includes a first diameter section over a portion of its length and a second diameter section which is larger than the first diameter section over another portion of its length, said second diameter section being sized for retention within an internal groove of the crystal holder.

7. The system as recited in claim 6, wherein said coiled conductive wire spring is made from electrically conductive wire.

8. The system as recited in claim 7, wherein said electrically conductive wire is selected from one of the group consisting of stainless steel, beryllium copper, nickel copper, piano wire, Inconel and molybdenum.

9. The system as recited in claim 1, wherein said flexible electrical contact comprises a tubular body having leaf springs disposed at respective ends of said tubular body.

10. The system as recited in claim 9, wherein the tubular body is defined by a first diameter section over a portion of its length and a second larger diameter section sized for retention within an internal groove of the crystal holder.

11. The system as recited in claim 10, wherein said tubular body is substantially hollow and includes at least one vent hole.

12. The system as recited in claim 1, wherein said retainer includes a split gap over its circumference enabling the retainer to reduce its effective diameter when compressed such that when said compressive force is released, said retainer is configured to engage an inner wall defining a bore of said crystal holder.

13. The system as recited in claim 1, wherein the retainer includes at least one external ear that loosely locks into position within an annular groove defined in an inner wall of said axial bore of the crystal holder.

14. The system as recited in claim 1, wherein the retainer maintains a light friction or close fit into a defined crystal bore of the crystal holder that provides modest level of crystal retention.

15. The system as recited in claim 1, wherein the retainer is made from an insulating material.

16. The system as recited in claim 1, wherein the insulating material is selected from the group consisting essentially of ceramics and resilient plastic.

17. A method for retaining a monitor crystal and providing electrical contact therewith for use in a deposition control monitor, said method comprising the steps of:
   providing a crystal holder having an axial bore and an annular seat sized for receiving a monitor crystal;
   providing a retainer disposed between the crystal holder and a sensor body, said retainer being at least partially disposed in said axial bore of said crystal bore and said sensor body including a fixed electrical contact engaged with an electrical measuring apparatus of the deposition control monitor; and
   providing a spanning electrical contact between a fixed electrical contact of said sensor body and one face of a retained crystal body such that the spanning electrical contact directly contacts both the fixed electrical contact and the face of the retained crystal body, wherein at least one of said crystal holder and said retainer includes at least one feature for maintaining said spanning electrical contact in a fixed orientation.

18. The method as recited in claim 17, wherein said spanning electrical contact is a coiled conductive spring, said conductive spring having a first diameter section over a portion of its length and a second diameter section over another section of its length which is larger than the first diameter section, said second diameter section being engageable in an interior groove formed in said retainer.

19. The method as recited in claim 17, wherein said retainer is substantially cylindrical and is defined by a split gap over it circumference, enabling said retainer to assume a smaller diameter, said outer diameter of said retainer being larger than the inner diameter of said crystal holder such that applying compressive force to said retainer permits said retainer to securely engage said crystal holder when attached thereto.

* * * * *